United States Patent
Cadieux et al.

(10) Patent No.: US 10,015,986 B2
(45) Date of Patent: Jul. 10, 2018

(54) ELECTRONIC VAPING DEVICE AND COMPONENTS THEREOF

(71) Applicant: Altria Client Services LLC, Richmond, VA (US)

(72) Inventors: Edmond J. Cadieux, Mechanicsville, VA (US); Douglas A. Burton, Glen Allen, VA (US); Patrick J. Cobler, Andover, MA (US); Barry S. Smith, Hopewell, VA (US); Peter Lipowicz, Midlothian, VA (US); Kai Cao, Somerville, MA (US)

(73) Assignee: Altria Client Services LLC, Richmond, VA (US)

( * ) Notice: Subject to any disclaimer, the term of this patent is extended or adjusted under 35 U.S.C. 154(b) by 148 days.

(21) Appl. No.: 14/805,944

(22) Filed: Jul. 22, 2015

(65) Prior Publication Data

US 2016/0021934 A1 Jan. 28, 2016

Related U.S. Application Data

(60) Provisional application No. 62/028,639, filed on Jul. 24, 2014.

(51) Int. Cl.
*A24F 47/00* (2006.01)
*A61M 11/04* (2006.01)
*A61M 15/06* (2006.01)

(52) U.S. Cl.
CPC .......... *A24F 47/008* (2013.01); *A24F 47/002* (2013.01); *A24F 47/004* (2013.01); *A61M 11/042* (2014.02); *A61M 15/06* (2013.01)

(58) Field of Classification Search
None
See application file for complete search history.

(56) References Cited

U.S. PATENT DOCUMENTS

2008/0257880 A1* 10/2008 Brown ................ A01M 1/2077
219/618
2012/0318882 A1* 12/2012 Abehasera .......... A61M 11/041
239/1

(Continued)

FOREIGN PATENT DOCUMENTS

| CN | 103689812 A | 4/2014 |
|----|-------------|--------|
| GB | 2504731 A | 2/2014 |
| WO | WO-2014048745 A1 | 4/2014 |

OTHER PUBLICATIONS

International Preliminary Report on Patentability for Application No. PCT/US2015/041511 dated Feb. 2, 2017.

(Continued)

*Primary Examiner* — Joseph S Del Sole
*Assistant Examiner* — Manley L Cummins, IV
(74) *Attorney, Agent, or Firm* — Harness, Dickey & Pierce, P.L.C.

(57) ABSTRACT

A cartomizer of an electronic vaping device includes a heater circuit which is located adjacent an air passage thereof. The heater circuit includes an electrically resistive heater in electrical communication with a secondary coil. A wick extends across the air passage. The wick is configured to draw pre-vapor formulation from a reservoir toward the heater. The heater is configured to heat the pre-vapor formulation to a temperature sufficient to vaporize the pre-vapor formulation and form a vapor. The cartomizer is connectable to a power supply component which includes a power source in electrical communication with a primary coil. The power supply component is configured to induce sufficient voltage in the secondary coil of the heater circuit such that the secondary coil is configured to heat the heater and vaporize the pre-vapor formulation when the primary coil is powered by the power source.

10 Claims, 5 Drawing Sheets

(56) References Cited

U.S. PATENT DOCUMENTS

| | | | | |
|---|---|---|---|---|
| 2014/0020697 A1* | 1/2014 | Liu | .................. | A24F 15/00 |
| | | | | 131/329 |
| 2014/0060528 A1* | 3/2014 | Liu | ................ | A24F 47/002 |
| | | | | 128/202.21 |
| 2015/0157756 A1* | 6/2015 | Duffield | ............ | A01M 1/2061 |
| | | | | 219/628 |
| 2015/0237918 A1* | 8/2015 | Liu | ................ | A24F 47/008 |
| | | | | 131/328 |
| 2015/0272219 A1* | 10/2015 | Hatrick | ............. | A24F 47/004 |
| | | | | 131/328 |

OTHER PUBLICATIONS

International Search Report PCT/ISA/210 for International Application No. PCT/US2015/041511 dated Oct. 7, 2015.
Written Opinion of the International Searching Authority PCT/ISA/237 for International Application No. PCT/US2015/041511 dated Oct. 7, 2015.
International Preliminary Report on Patentability for Application No. PCT/US2015/041511 dated Jul. 22, 2015.

* cited by examiner

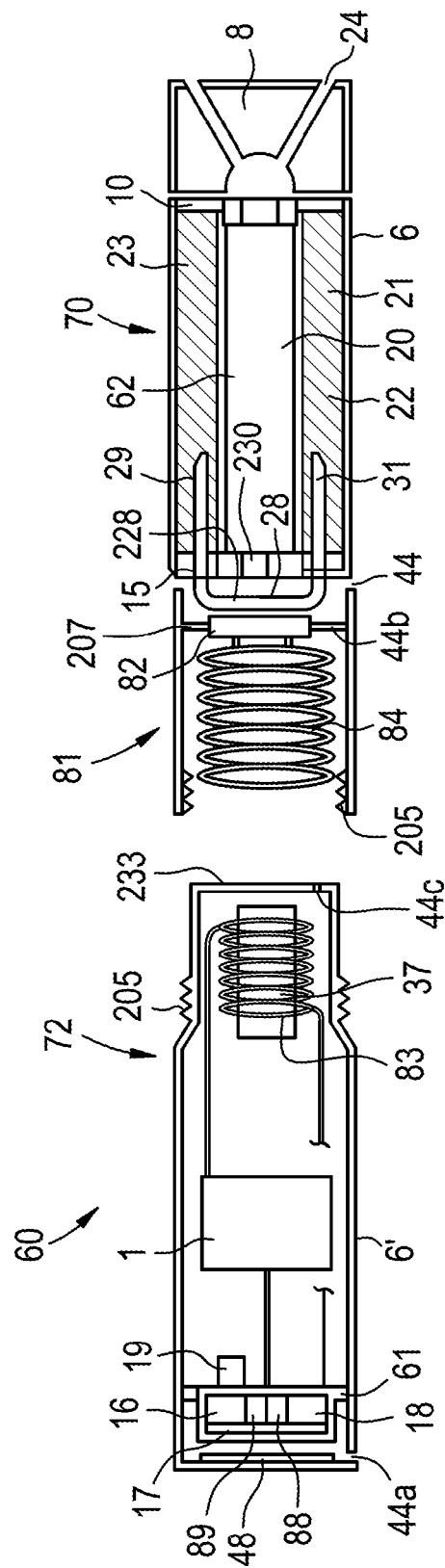

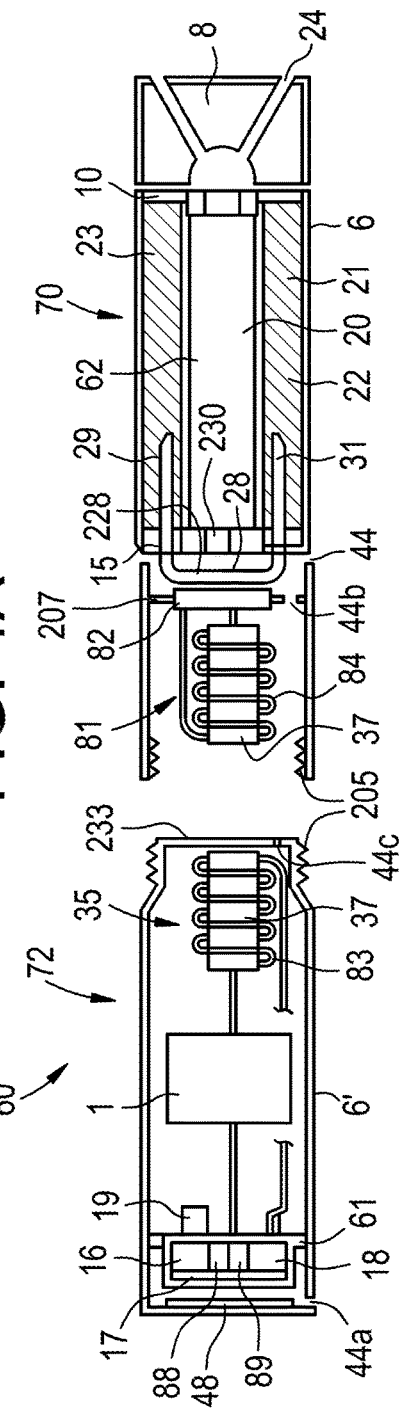
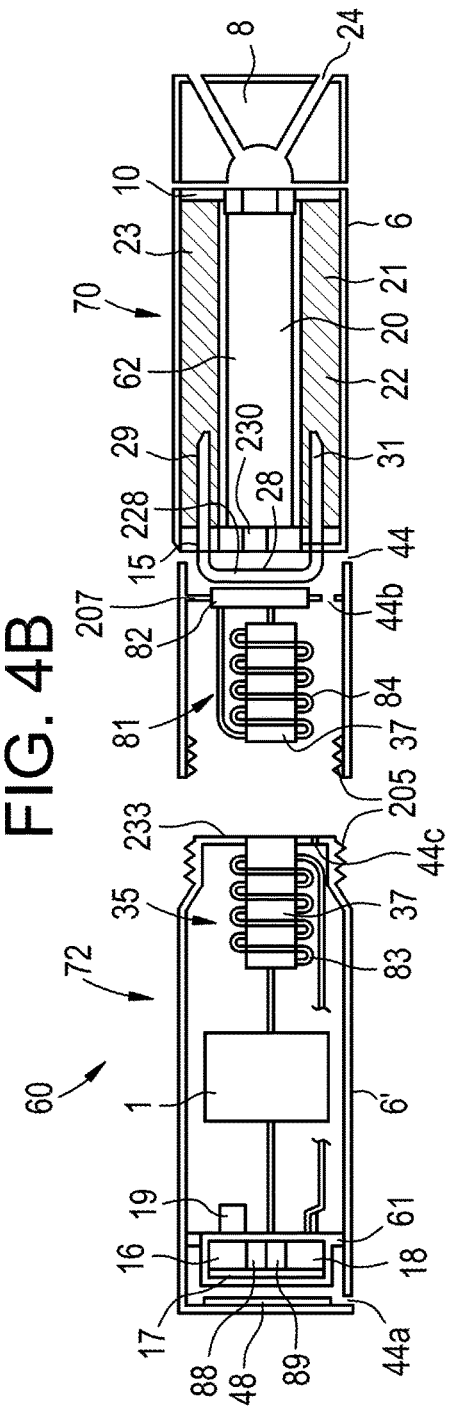

ELECTRONIC VAPING DEVICE AND COMPONENTS THEREOF

PRIORITY STATEMENT

This application is a non-provisional application that claims priority to U.S. provisional app. No. 62/028,639, filed on Jul. 24, 2014, the entire content of which is incorporated by reference in its entirety.

BACKGROUND

Field

The present disclosure relates to electronic vaping devices including electrically resistive heaters.

Description of Related Art

Electronic vaping devices may include a first section coupled to a second section via a threaded connection. The first section may be a replaceable cartridge, and the second section may be a reusable fixture. The first section may include a reservoir containing a pre-vapor formulation. A wick draws the pre-vapor formulation from the reservoir towards a heater that heats the pre-vapor formulation to a temperature sufficient to vaporize the pre-vapor formulation.

SUMMARY

In at least one example embodiment, a cartomizer of an electronic vaping device is provided.

In at least one example embodiment, the cartomizer includes an outer housing extending in a longitudinal direction, an air inlet, a vapor outlet, an air passage communicating with the air inlet and the vapor outlet, and a reservoir. A heater circuit is located adjacent the air passage. The heater circuit includes an electrically resistive heater in electrical communication with a secondary coil. A wick extends across the air passage and is in communication with the reservoir. The wick is configured to draw pre-vapor formulation from the reservoir toward the heater.

In some example embodiments, the cartomizer is configured to connect with a power supply component which includes a power source in electrical communication with a primary coil that induces voltage in the secondary coil of the heater circuit to heat the heater to a temperature sufficient to vaporize the pre-vapor formulation and form a vapor in the air passage.

In at least one example embodiment, an electronic vaping device includes a cartomizer and a power supply component. The cartomizer includes an outer housing extending in a longitudinal direction, an air inlet, a vapor outlet, an air passage communicating with the air inlet and the vapor outlet, a reservoir, a heater circuit located adjacent the air passage, the heater circuit including an electrically resistive heater in electrical communication with a secondary coil, and a wick extending across the air passage, in communication with the reservoir, and configured to draw pre-vapor formulation from the reservoir towards the heater. The power supply component includes a power source in electrical communication with a primary coil. The primary coil is configured to induce voltage in the secondary coil of the heater circuit.

In some example embodiments, the primary coil is axially separated from a proximate end of the secondary coil when the cartomizer is connected to the power supply component. In at least one example embodiment, the primary coil is surrounded by the secondary coil when the cartomizer is connected to the power supply component. In other example embodiments, the secondary coil is surrounded by the primary coil when the cartomizer is connected to the power supply component. In some example embodiments, the primary coil is a helix extending in one of the longitudinal direction of the second outer housing and a transverse direction to the longitudinal direction of the second outer housing. In at least one example embodiment, the primary coil is a planar coil. In another example embodiment, the heater has a greater electrical resistance than the secondary coil.

In some example embodiments, the heater is a coil heater wound about the wick. In other example embodiments, the heater is a ribbon of electrically resistive and conductive mesh material wound about the wick. In another example embodiment, the heater is an electrically resistive and conductive rod extending through filaments of the wick. In another example embodiment, the heater is a portion of an electrically resistive and conductive mesh which is integral with the wick.

In at least one example embodiment, the heater is an electrically resistive and conductive plate disposed in contact with a portion of the wick wherein pre-vapor formulation is desired to be vaporized. In some example embodiments, the heater comprises at least one material selected from the group consisting of stainless steel, copper, copper alloys, ceramic material coated with film resistive material, nickel chromium alloys, iron oxide, and combinations thereof.

In at least one example embodiment, the power supply component includes control circuitry including a puff sensor. The puff sensor is configured to sense a pressure drop and initiate power from the power source to the primary coil such that voltage is induced in the secondary coil of the heater circuit. The power supply of the power supply component is a battery. In some example embodiments, the power supply component includes control circuitry including a rectifier circuit and a storage circuit. The rectifier circuit is configured to rectify a voltage induced in the primary coil such that the storage circuit may charge the battery when the primary coil is within an inductive field.

In at least one example embodiment, the cartomizer is connected to the power supply component with a mechanical or magnetic connection. In some example embodiments, the cartomizer is a disposable downstream section and the power supply component is a reusable upstream section. In at least one example embodiment, at least one of the heater and the secondary coil are made of a magnetic material.

In some example embodiments, the electronic vaping device may include an inner tube within the outer housing. The inner tube defines the air passage which communicates with the inlet and the outlet. The air passage is a central air passage. The pre-vapor formulation is contained in an annular space between the outer housing and the inner tube.

In some example embodiments, a method of producing a vapor from an electronic vaping device is provided. The method includes wicking a portion of a pre-vapor formulation from a reservoir to a location adjacent an inlet portion of an air passageway and in proximity to a heater circuit including a heater and a secondary coil, the secondary coil positioned in proximity to a primary coil of a power supply, generating a signal indicative of a puff by communicating a draw upon the electronic vaping device, and vaporizing at least some of said wicked portion of said pre-vapor formulation by applying an oscillating power cycle to the primary coil responsively to the generated signal so as to induce voltage in the secondary coil such that the heater is sufficiently heated to volatilize at least some of the wicked portion of the pre-vapor formulation and drawing the volatilized pre-vapor formulation through the air passageway and the electronic vaping device. The drawing of the volatilized formulation may be along a straight air passageway.

BRIEF DESCRIPTION OF THE DRAWINGS

The various features and advantages of the non-limiting example embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 3 is a cross-sectional view of an electronic vaping device according to some example embodiments.

FIGS. 4A and 4B are cross-sectional views of electronic vaping devices according to some example embodiments.

DETAILED DESCRIPTION

Figure 1:
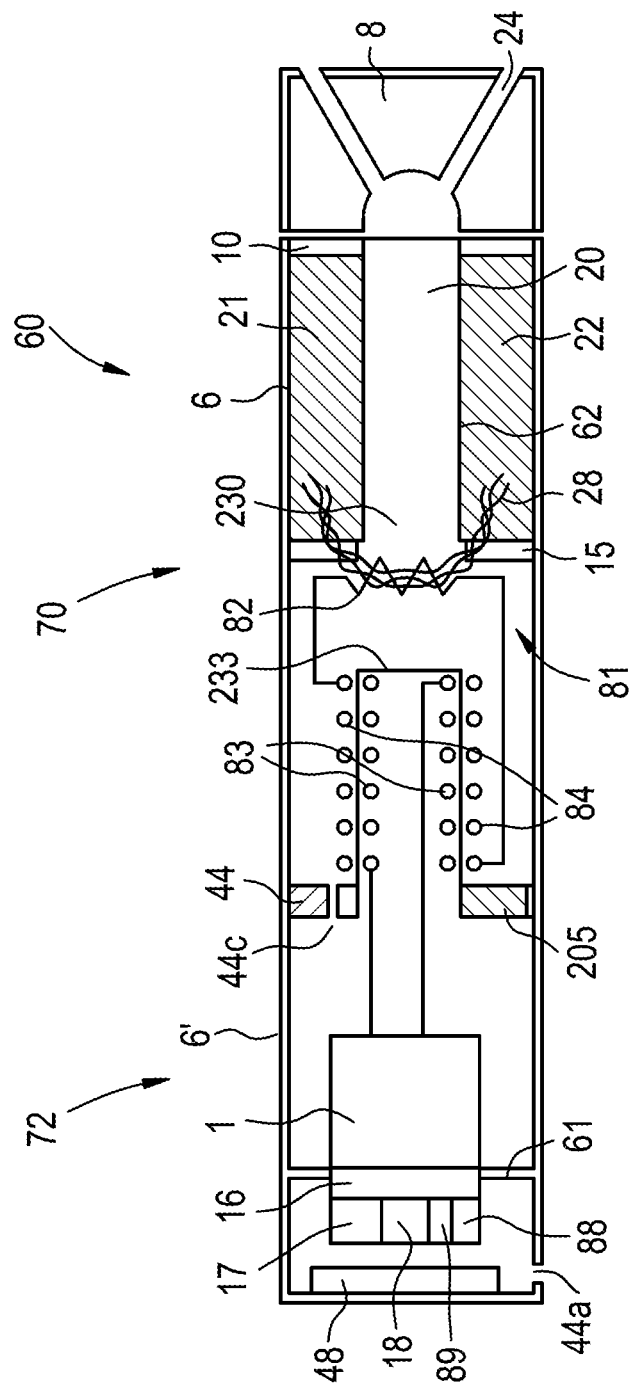
FIG. 1 is a cross-sectional view of an electronic vaping device according to some example embodiments.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of the example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Disclosed herein are example embodiments of an electronic vaping device 60. Referring to FIG. 1, the electronic vaping device 60 comprises a cartomizer (first section) 70 and a power supply component (second section) 72. A heater circuit 81 is disposed in the cartomizer 70 wherein the heater circuit 81 includes an electrically resistive heater 82 and a secondary coil 84. The battery section 72 includes a control circuitry (or chip) 16, a puff sensor 17, and a power (delivery or transfer) circuit comprising a power source 1 and a primary coil 83 in electrical communication with the power source 1 via the puff sensor 17 and control circuitry 16. The heater circuit 81 cooperates with a power delivery circuit of the power supply component 72. The power source 1 is in electrical communication with the primary coil 83 such that the electrically resistive heater 82 is configured to heat and vaporize pre-vapor formulation from a wick 28, which draws the pre-vapor formulation from a reservoir 22 of the cartomizer 70.

The cartomizer 70 may be disposable, and the cartomizer 70 may be connectable to the power supply component 72 at a connection (connector) 205. For example, the connection 205 may be a threaded connection or another convenience such as a snug-fit, detent, clamp, clasp and/or magnetic connection. In some example embodiments, the cartomizer 70 and the power supply component 72 may be an integral electronic vaping device 60, which is disposable.

Upon closure of the connection 205, the primary coil 83 is configured to generate an oscillating inductive, electromagnetic field, when powered by the power source 1, which induces sufficient voltage in the secondary coil 84, thereby driving the heater circuit 81, and causing the electrically resistive heater 82 to heat. Thus, the primary coil 83 and the secondary coil 84 are magnetically coupled such that a change in current through the primary coil 83 induces a voltage across the secondary coil 84 through electromagnetic induction. The coupling can be increased by placing the primary coil 83 and the secondary coil 84 close together and/or on a common axis.

In at least one example embodiment, the primary coil 83 and the secondary coil 84 are physically oriented with respect to each other in a manner such that the efficiency of power transferred therebetween is increased so as to reduce the amount of power required to resistively heat the electrically resistive heater 82. Further, the primary coil 83 and the secondary coil 84 each include a desired (or, alternatively a predetermined) number of turns in the respective coils thereof such that the efficiency of power transferred therebetween is increased so as to reduce the amount of power required to resistively heat the electrically resistive heater 82.

Figure 2A:
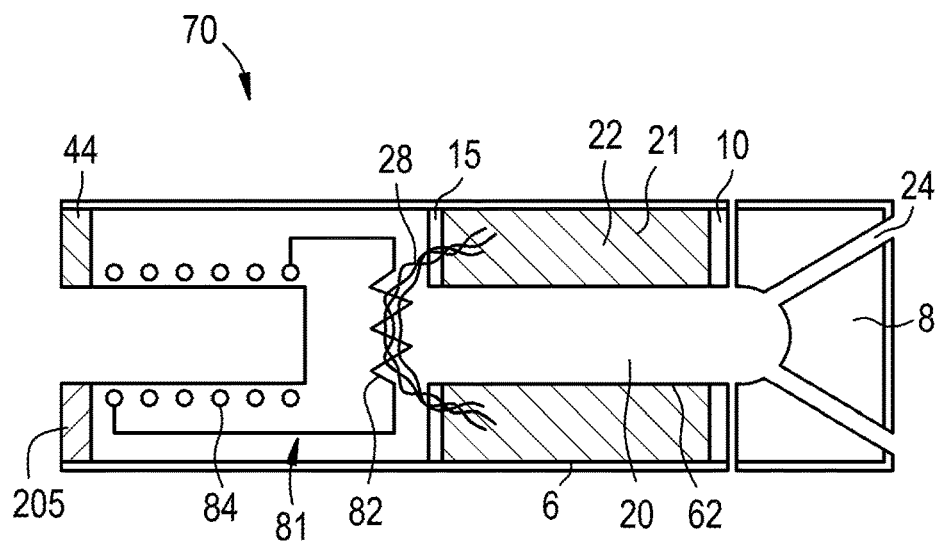
FIG. 2A is a cross-sectional view of a cartomizer of an electronic vaping device according to some example embodiments.

Referring to FIG. 1, as well as FIG. 2A which illustrates a replaceable cartomizer 70, the cartomizer 70 comprises an outer housing 6 (such as a cylindrical outer tube) which extends longitudinally and one or more air inlets 44. An inner tube 62 disposed within the outer housing 6 defines a straight, central air passage 20, which communicates with the one or more air inlets 44 and one or more vapor outlets 24. The one or more vapor outlets 24 may be in a mouth-end insert or mouthpiece 8. The mouth-end insert 8 may be a multi-port mouth-end insert. There are two air inlets 44 which communicate with the central air passage 20. In some example embodiments, there may be three, four, five or more air inlets 44. If there are more than two air inlets, the air inlets 44 are located at different locations along the length and/or around the circumference of the electronic vaping device 60. Further, altering the size and number of air inlets 44 may also aid in establishing a desired resistance to draw of the electronic vaping device 60.

In some example embodiments, the cartomizer 70 includes a mouth-end insert 8 having two or more, off-axis, diverging vapor outlets 24, or four of such outlets 24. In some example embodiments, the mouth-end insert 8 may have a single outlet 24. The mouth-end insert 8 is in fluid communication with the central air passage 20 defined by the interior of inner tube 62.

Locating the heater 82 adjacent an inlet portion 230 of the central channel 20 promotes fuller vapor formation by providing a generally straight flow path from the location of the heater 82 to the interior of the multi-port mouth-end insert 8. Such an arrangement avoids or lessens abrupt changes in direction of flow, and avoids or lessens associated losses due to impaction and other effects which would otherwise impede vapor development and production. Also the central air passage 20 minimizes or lessens contact and thermal transfer between the vapor and the walls of the reservoir 22 formed by the inner tube 62.

Each air inlet 44 comprises a beveled entrance and an angled passageway. In some example embodiments, the electronic vaping device 60 includes a pair of air inlets 44. Each of the air inlets 44 is angled toward the mouth-end insert 8 of the electronic vaping device 60 at an angle in the range of about 35° to about 55° with respect to the longitudinal axis of the article 60, or at an angle in the range of about 40° to about 50°. In some example embodiments, each of the air inlets 44 is angled toward the mouth-end insert 8 at an angle of about 45°. Such arrangement minimizes (abates) and/or reduces "whistling" noise during a draw on the electronic vaping device 60.

A reservoir 22 is established or provided in an annular space between the outer housing 6 and the inner tube 62, wherein the annular space is sealed at an upstream end by an upstream seal 15 and at a downstream location by a downstream seal (or stopper) 10. The reservoir 22 contains a pre-vapor formulation, and optionally, a storage medium 21 (i.e., fibrous medium) configured to disperse the pre-vapor formulation in the reservoir 22.

A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol.

Also, the pre-vapor formulation has a boiling point suitable for forming a vapor during vaping. If the boiling point is too high, the heater 82 will not be able to vaporize pre-vapor formulation in the wick 28. However, if the boiling point is too low, the pre-vapor formulation may vaporize prematurely without the heater 82 being activated.

The storage medium 21 may be a wrapping of gauze about the inner tube 62. The storage medium 21 comprises an outer wrapping of gauze surrounding an inner wrapping of gauze of the same or different material. In one example embodiment, the storage medium 21 of the reservoir 22 is constructed from an alumina ceramic in the form of loose particles, loose fibers, or woven or nonwoven fibers, or alternatively the storage medium 21 is constructed from a cellulosic material such as cotton or gauze material or polymer material, such as polyethylene terephthalate, in the form of a woven fabric or alternatively the polymer material may be in the form of a bundle of loose fibers.

The storage medium 21 may comprise a fibrous material, for example, cotton, polyethylene, polyester, rayon, etc. and combinations thereof. The fibers may have a diameter ranging in size from about 6 microns to about 15 microns (e.g., about 8 microns to about 12 microns or about 9 microns to about 11 microns). The storage medium 21 may be a sintered, porous, or foamed material. Also, the fibers are sized to be irrespirable and may have a cross-section which has a y-shape, cross shape, clover shape, or any other suitable shape. In some example embodiments, the reservoir 22 may comprise a pre-vapor formulation filled tank lacking a storage medium 21.

The heater circuit 81, which includes the electrically resistive heater 82 and the secondary coil 84, is located adjacent an upstream portion of the central air passage 20 of the cartomizer 70. The filamentary wick 28 is in contact with the pre-vapor formulation in the reservoir 22. The wick 28 is configured to draw pre-vapor formulation from the reservoir 22 into a proximate relation with the electrically resistive heater 82. When the heater circuit 81 is driven by the oscillating electromagnetic field produced by the primary coil 83, the electrically resistive heater 82 heats the pre-vapor formulation to a temperature sufficient to vaporize the pre-vapor formulation and produce a vapor. Accordingly, the wick 28 and the electrically resistive heater 82 may be referred to as a vaporizer. The electrically resistive heater 82 is located within the cartomizer 70 proximate to and superposing at least a portion of an upstream inlet portion 230 of the central air passage 20.

In at least one example embodiment, as illustrated in FIGS. 1 and 2A, the heater 82 comprises a wire coil which at least partially surrounds the wick 28. The wire coil may extend fully or partially around the circumference of the wick 28 with or without spacing between the turns of the coil. In another example embodiment, the heater coil is not in contact with the wick 28. Alternatively, the heater 82 may be a conductive rod extending through filaments of the wick 28, or any suitable means for heating pre-vapor formulation delivered to a proximate location thereto. The heater 82 has a greater electrical resistance than the secondary coil 84 such that the secondary coil 84 does not overheat during operation of the electronic vaping device 60.

Figure 5:
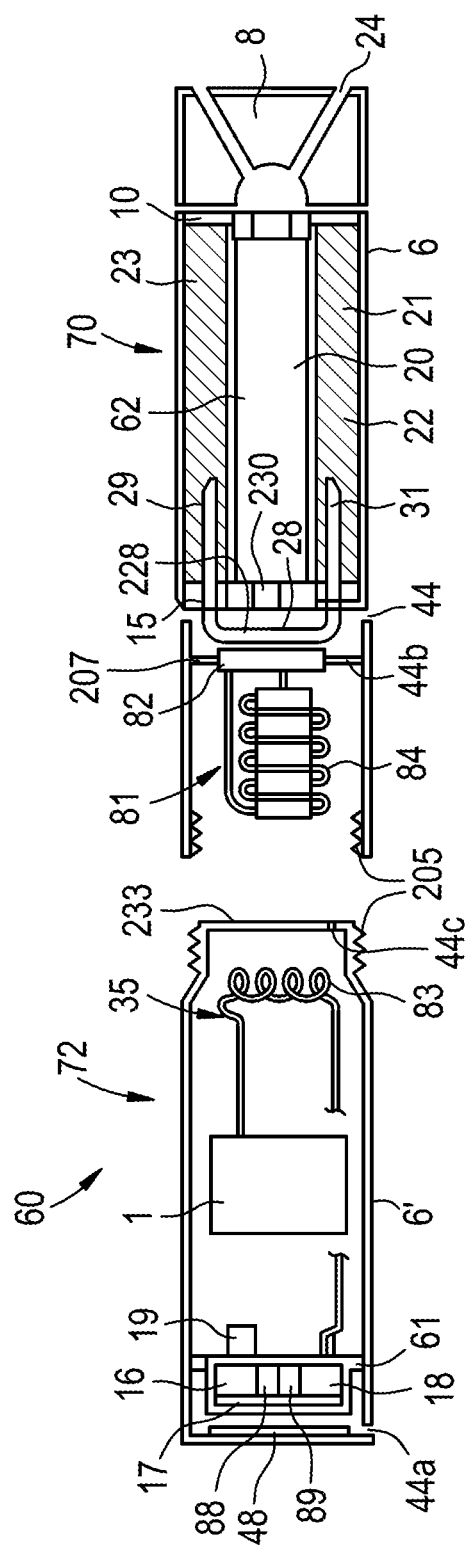
FIG. 5 is a cross-sectional view of an electronic vaping device according to some example embodiments.

In at least one example embodiment, as illustrated in FIGS. 3-5, which will be described in greater detail below, the electrically resistive heater 82 may be in the form of a thin disc or foil of electrically conductive and electrically resistive material.

Referring now to FIGS. 1-5, the materials of the electrically resistive heater 82, the primary coil 83, and the secondary coil 84 are metallic and optionally magnetic. Examples of suitable electrically resistive/conductive (i.e., electrically resistive and conductive) materials that may be used to form the electrically resistive heater 82 include metals, alloys, and superalloys. For example, metals such as but not limited to nickel, cobalt, chromium, aluminium, titanium, zirconium, hafnium, niobium, molybdenum, tantalum, tungsten, tin, gallium, manganese, iron, platinum, osmium, iridium, ruthenium, rhodium, palladium, copper, and alloys thereof, may be used to form the heater 82. The heater 82 comprises at least one material, for example, stainless steel, copper alloys, nickel-chromium alloys, cobalt alloys, superalloys, etc. and combinations thereof. In an alternate example embodiment, for example, the heater 82 may be formed of nickel aluminides, a material with a layer of alumina on the surface, iron aluminides, iron oxide, and other composite materials. The electrically resistive/conductive material may optionally be embedded in, encapsulated or coated with an insulating material or vice-versa, depending on the kinetics of energy transfer and the external physicochemical properties required.

In at least one example embodiment, the heater 82 is formed of nickel-chromium alloys or iron-chromium alloys. In another example embodiment, the heater 82 may be a ceramic composite heater having an electrically resistive/conductive layer on an outside surface thereof. In another example embodiment, the electrically resistive/conductive layer may be embedded in the ceramic heater.

In another example embodiment, the heater 82 may be constructed of an iron-aluminide (e.g., FeAl or $Fe_3Al$), such as those described in U.S. Pat. No. 5,595,706 to Sikka et al., or nickel aluminides (e.g., $Ni_3Al$), the entire content of which is incorporated herein by reference thereto.

When in the form of a metallic disc or foil, the heater 82 may be about 3 millimeters (mm) to about 8 mm wide and about the thickness of household aluminum foil.

The wick 28 may be constructed of a flexible, filamentary material. Alternatively, the wick 28 may be a porous body, or any suitable means for delivering pre-vapor formulation to a location proximate to a heater. The wick 28 may comprise a plurality of filaments having sufficient capillarity via interstitial spaces between the filaments to draw pre-vapor formulation from the reservoir 22. In some example embodiments, the wick 28 comprises a bundle of such glass, ceramic, or metal filaments or windings of filaments wound together into separate bundles or strands, wherein the wick 28 comprises a plurality of such bundles, such as three or more bundles or strands of wound fiberglass filaments.

The wick 28 may include filaments having a cross-section which is generally cross-shaped, clover-shaped, Y-shaped, or in any other suitable shape.

The wick 28 includes any suitable material or combination of materials. Examples of suitable materials are glass filaments, fiberglass filaments, and ceramic, metal, or graphite based materials. Moreover, the wick 28 may have any suitable capillarity to accommodate pre-vapor formulations having different physical properties such as density, viscosity, surface tension and vapor pressure. The capillarity properties of the wick 28 and the properties of the pre-vapor formulation are selected such that the wick 28 is always wet in the area adjacent the heater 82 to avoid overheating of the heater 82 and/or the wick 28.

In at least one example embodiment, the wick arrangement aids in protecting the pre-vapor formulation in the reservoir 22 from oxygen (because oxygen may not generally enter the storage portion via the wick) so that the risk of degradation of the pre-vapor formulation is significantly reduced. Moreover, by using an opaque outer housing 6, the reservoir 22 is protected from light so that the risk of degradation of the pre-vapor formulation is significantly reduced. Thus, a high level of shelf-life and cleanliness may be maintained.

Figure 2B:
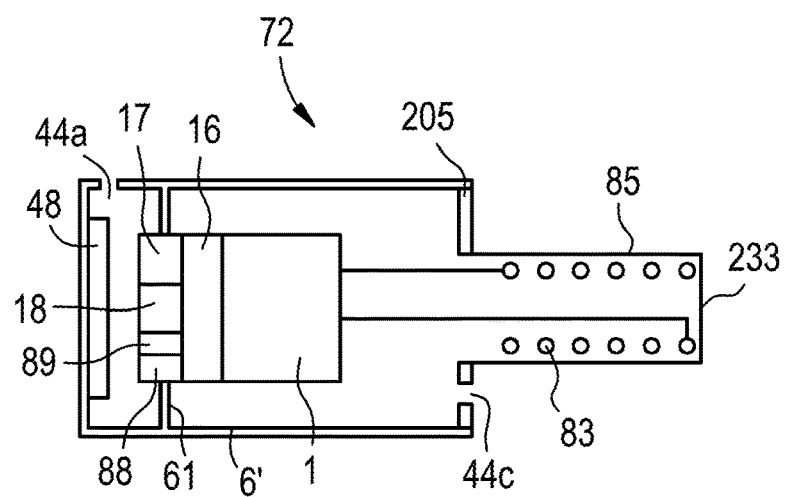
FIG. 2B is a cross-sectional view of a reusable power supply component of an electronic vaping device according to some example embodiments.

Referring to FIG. 1, as well as FIG. 2B which illustrates a battery section or a power supply component 72, which may be reusable, the battery section 72 comprises an outer housing 6' (second outer housing) extending in a longitudinal direction and includes a power source or battery 1 in electrical communication with a primary coil 83 through control circuitry 16.

Referring to FIGS. 1-5, the power supply component 72 may include a seal end 233 adjacent the connection 205 so as to protect the electronic contents of the cartomizer 70 from external elements. The seal end 233 of the power supply component 72 is inserted into an opening of the cartomizer 70 such that the primary coil 83 is nested within the secondary coil 84 when the power supply component 72 and the cartomizer 70 are assembled together (see FIGS. 1 and 3). In an alternate example embodiment, the secondary coil 84 may be configured to be nested within the primary coil 83.

Referring to FIGS. 1, 2B, and 3-5, the power source 1 may include a battery arranged in the electronic vaping device 60. A battery anode connector may connect the anode of the battery with one pole of the primary coil 83. A battery cathode connector may connect the cathode of the battery with another pole of the primary coil 83 such that an inductive field may be generated to thereby induce voltage in the secondary coil 84. The primary coil 83 generates an inductive field and induces voltage in the secondary coil 84, which is disposed in the inductive field of the primary coil 83, to thereby power the heater 82, which forms the heater circuit 81 with the secondary coil 84.

The battery or power source 1 may be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, the electronic vaping device 60 is vapable by an adult vaper until the energy in the power source 1 is depleted. Alternatively, the power source 1 may be rechargeable and include circuitry allowing the battery to be chargeable by an external charging device. In that case, the circuitry, when charged, provides power for a pre-determined number of puffs, after which the circuitry must be re-connected to an external charging device.

In at least one example embodiment, the control circuitry 16 includes an oscillator 18 which is configured to oscillate the power supplied to the primary coil 83, such that the latter generates an oscillating inductive field in a desired direction and time period and the primary coil 83 induces voltage in the secondary coil 84 of the heater circuit 81 of the cartomizer 70 to cause the heater 82 to heat to a desired (or, alternatively a predetermined) temperature and for a desired (or, alternatively a predetermined) time period.

The control circuitry 16 may also include a voltage regulator 19 such that the voltage across the primary coil 83 is controlled. The primary coil 83 is powered by the power source 1 via the oscillator 18 at a frequency of about 100 kHz to 1 MHz. The frequency is selected based upon parameters of the primary coil 83, parameters of the secondary coil 84, parameters of the heater 82, and the relationship between the primary coil 83 and the secondary coil 84. In the case of a primary coil 83 and a secondary coil 84 those parameters may include, but are not limited to, the type of material, the spacing between turns, the number of turns, the diameter of the coil, and the length the coil spans. The frequency may also depend upon the characteristics of a ferrite core 37 about which the primary coil 83 may be wound (see FIG. 3) or upon the characteristics of respective ferrite cores 37 about which the primary coil 83 and the secondary coil 84 may be individually wound (see FIGS. 4A and B).

The control circuitry 16 communicates responsively with a puff sensor (pressure sensor) 17 that is located at a distal end portion of the battery section 72. The puff sensor 17 is configured to generate a signal responsive to air being drawn from the electronic vaping device 60 through the mouth-end insert 8. In response to the signal from the puff sensor 17, the control circuitry 16 communicates an oscillating power cycle to the primary coil 83 which induces a voltage in the secondary coil 84 of the heater circuit 81 to thereby cause the heater 82 to heat. The pressure drop of a draw (or puff) upon the mouth-end insert 8 of cartomizer 70 is communicated to the puff sensor 17 through openings 44b and 44c in components 70 and 72 (see FIGS. 3-5), respectively, adjacent the connector 205, and via spaces provided between the battery 1 and adjacent portions of the housing 6'.

A partition 61 is provided at or upstream of the puff sensor 17 to isolate a pressure relief inlet 44a, which is located at the distal end of the battery section 72. The pressure relief inlet 44a serves to relieve pressure on a side of the puff sensor 17 at which the pressure relief inlet 44a is located. If pressure is not relieved, the pressure may interfere with facile operation of the puff sensor 17. In at least one example embodiment, the puff sensor 17 and control circuitry 16 may be a single chip. The chip may be an integrated circuit with resistors and timing circuits. The chip may also include inputs and outputs, which may function to cause switching (i.e., supply power from the power source 1 to the primary coil based on the puff sensor signal, and to cause the LED to blink when power is low, etc.).

The control circuitry 16 may be configured to provide a power cycle having elements that achieve improved or optimal ramp-up in temperature of the heater 82 and maintenance of an operating temperature for a desired (or, alternatively a predetermined) period of time. For example, the power cycle may be divided into two (or more) phases each having a respective time period of T1 and T2. In the first phase (T1), a higher frequency and magnitude of oscillation may be employed so as to cause the heater 82 to heat rapidly. In the second phase (T2), the control circuitry 16 may provide a power cycle with a more moderate frequency and/or a more moderate magnitude of oscillation so as to achieve steady heating effect throughout the second phase (T2). Through testing, analytics, and/or modeling, a desired power cycle may be empirically established. The power cycles could include a plurality of phases wherein only the amplitude or only the frequency is varied and may include phases wherein there is no power and/or oscillation being directed to the primary coil 83.

The control circuitry 16 may control the primary coil 83 such that an alternating inductive field is generated. In an alternate example embodiment, the control circuitry 16 may pulse the primary coil 83 between an on and off state such that the generated inductive field may intermittently induce voltage in the secondary coil 84 to thereby intermittently power the heater 82. The pulsing may control the temperature of the heater 82 and vapor production.

The control circuitry 16 is also configured to adjust frequency, magnitude, and/or time period responsive to readings of battery voltage so that consistent performance is maintained as the voltage level of the battery 1 declines during vaping.

In at least one example embodiment, the control circuitry 16 includes a microprocessor and a computer-readable storage medium. The microprocessor may be coupled to the computer-readable storage medium. The computer-readable storage medium may store at least one look up table and other information for reference by the microprocessor. The look up tables can include battery voltage readings mapped to possible frequencies, magnitudes, and/or time periods that may be empirically established. The control circuitry 16 may sense a battery voltage and access the look up table stored in the computer-readable storage medium to obtain control parameters including desired frequency, magnitude, and/or time period based on battery voltage.

For example, the control circuitry 16 may sense a battery voltage and based on the battery voltage, determine and/or set a desired frequency and magnitude for the first time phase T1 and the second time phase T2.

In at least one example embodiment, the puff sensor 17 is configured to generate more than one signal, such as a range of signals responsive to the magnitude of a puff or draw upon the mouth-end insert 8 so that the control circuit 16 may discriminate between the signals to adjust the frequency, magnitude, and/or time of the immediate power cycle in response to the signal the control circuit 16 receives from the puff sensor 17. For instance a heavy draw might generate a first signal from the puff sensor 17, which in turn would cause the control circuitry to extend the time of the immediate power cycle responsively or make some other adjustment in the power cycle to provide a greater production of vapor.

When activated, the heater 82 heats a portion of the wick 28 surrounded by the heater for less than about 10 seconds. In some example embodiments, the heater 82 heats a portion of the wick 28 for less than about 7 seconds. Thus, the power cycle (or maximum puff length) may range in period from about 2 seconds to about 10 seconds (e.g., about 3 seconds to about 9 seconds, about 4 seconds to about 8 seconds or about 5 seconds to about 7 seconds).

In some example embodiments, the control circuitry 16 may include a manually configured switch for an adult vaper to initiate a puff. The time-period and characteristics of the electric current supply to the primary coil 83 may be pre-set depending on the amount of pre-vapor formulation desired to be vaporized. The control circuitry 16 may be pre-programmed or programmable for this purpose. Alternatively, the circuitry 16 may supply power to the primary coil 83 as long as the puff sensor 17 detects a pressure drop.

The control circuitry 16 may also include a light emitting diode (LED) 48 configured to glow when the heater 82 is activated. The LED 48 is at an upstream (distal) end of the electronic vaping device 60 so that the LED 48 mimics the appearance of a burning coal during a puff. The LED 48 may be arranged to be visible to the adult vaper. In addition, the LED 48 may be utilized for system diagnostics of the electronic vaping device 60. The LED 48 may also be configured such that the adult vaper may activate and/or deactivate the LED 48 for privacy. For example, the adult vaper may choose to deactivate the LED 48, such that the LED 48 would not activate during vaping if desired.

The control circuitry 16 may also include a rectifier circuit 88 and a storage circuit 89 for recharging the battery 1 when the power supply component 72 is disposed within an inductive field. The rectifier circuit 88 is configured to rectify a voltage induced in the primary coil 83 such that the storage circuit 89 may charge the battery 1 when the primary coil 83 is within an inductive field. In at least one example embodiment, the battery 1 of the power supply component 72 may be recharged alone by placing the power supply component 72 in an inductive field, or alternatively, the power supply component 72 may be assembled with the cartomizer 70 wherein the control circuitry may enter a recharge mode when the entire electronic vaping device 60 is placed within an inductive field.

Having a separate cartomizer 70 and power supply component 72 allows the heater 82 of the heater circuit 81, wick 28, and reservoir 22, which are in contact with the pre-vapor formulation to be disposed of when the cartomizer 70 is depleted, and allows the power supply component 72 to be reusable. Thus, there will be no cross-contamination between different mouth-end inserts 8, for example, when using different pre-vapor formulations. Also, if the cartomizer 70 is replaced at suitable intervals, there is little chance of the heater 82 and/or wick 28 becoming clogged with pre-vapor formulation. Further, by providing an arrangement wherein no wires physically connect the power source 1 of the power supply component 72 to the heater 82 in the cartomizer 70 a simple assembly may be formed which reduces the cost of manufacture of the electronic vaping device 60.

In some example embodiments, the electronic vaping device 60 is about the same size as a cigarette. In some example embodiments, the electronic vaping device 60 may be about 80 mm to about 110 mm long or about 80 mm to about 100 mm long, and about 10 mm or less in diameter. For example, in at least one example embodiment, the electronic vaping device is about 84 mm long and has a diameter of about 7.8 mm. In another example embodiment, the electronic vaping device may have an outer diameter of about 10 mm and an inner diameter of about 9.5 mm. In some example embodiments, the electronic vaping device 60 may be in a size and form approximating a cigar or a pipe.

The outer housing 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. The material may be light and non-brittle.

Some example embodiments of the electronic vaping device are described as being cylindrical. In other example embodiments, the electronic vaping device may have other suitable forms including right angular, triangular, oval, oblong, or other cross-sections.

The electronic vaping device is described herein and may be of any form, size and shape, including electronic cigarettes, cigars, pipes, hookahs, and the like.

Referring to FIGS. 3-5, in at least one example embodiment, the wick 28 includes a transverse middle portion 228, which extends across (is adjacent to) the upstream seal 15 and the upstream (inlet) portion 230 of the central air passage 20, and includes a first end portion 29 and also a second end portion 31, which extend longitudinally through the upstream seal 15 into the confines of the reservoir 22 so as to be in contact with pre-vapor formulation in the reservoir 22. Notches are provided at locations along the perimeter of the upstream seal to accommodate placement of the end portions 29, 31 of the wick 28. In some example embodiments, the wick 28 may include only one end portion 29 in communication with the reservoir. The placement and routing of the portions of the wick 28 may be other than as specifically described, so long as pre-vapor formulation is drawn from the reservoir 22 into proximate relation with the heater 82, wherever located.

In some example embodiments, as shown in FIGS. 3-4B, the primary coil 83 further includes a cylindrical core comprising a ferrite material 37. The primary coil 83 is wound about the core 37 and the core 37 extends in the longitudinal direction of the first and/or second outer housing 6, 6' and/or in a transverse direction perpendicular to the longitudinal direction of the first and/or second outer housing 6, 6'.

In some example embodiments, a support 207 supports the heater 82 within the cartomizer 70 in a fixed location relative to the wick 28 and/or the connector 205.

In at least one example embodiment, for example as illustrated in FIGS. 3-4B, the axis of symmetry of the primary coil 83 and respective optional ferrite core 37, and the axis of symmetry of the secondary coil 84 and respective optional ferrite core 37, extends in the longitudinal direction of the outer housing 6'.

In at least one example embodiment, as shown in FIG. 3, when the first section 70 and the second section 72 are connected, the primary coil 83 is nested within the secondary coil 84, such that the primary coil 83 is substantially surrounded by the secondary coil 84. In other example embodiments, the primary coil 83 may at least partially surround the secondary coil 84.

In the case wherein each of the primary coil 83 and the secondary coil 84 are wound about respective ferrite cores 37, as shown in FIGS. 4A and 4B, adjacent ends of the ferrite cores 37 and the respective primary and secondary coils 83, 84 are arranged to face each other, align, and/or abut when the cartomizer 70 is assembled with the power supply component 72. In some example embodiments, the primary coil 83 may be axially separated from a proximate end of the secondary coil 84 when the cartomizer 70 is connected to the power supply component 72.

In at least one example embodiment, as illustrated in FIG. 4B, the ferrite core 37 of the power supply component 72 might be flush with the seal end 233 so that opposing ends of the ferrite cores 37 of the power supply section 72 and the cartomizer 70 are exposed and come into mutual contact upon closure of the connector (connection) 205.

In a further example embodiment, for example as illustrated in FIG. 5, the axis of symmetry of the primary coil 83 and the secondary coil 84 may be oriented transverse to the longitudinal axis of the electronic vaping device 60. In an additional example embodiment, both the primary coil 83 and the secondary coil 84 may be planar coils, which are arranged to face each other, align, and/or abut.

When sufficient voltage is induced in the secondary coil 84, the heater 82 is configured to heat pre-vapor formulation drawn theretoward by the wick 28 to a temperature sufficient to vaporize the pre-vapor formulation and form a vapor in the central air passage 20. The heater 82 is in thermal communication with the wick 28 and heats pre-vapor formulation in the wick 28 by thermal conduction. Alternatively, heat from the heater 82 may be transferred to a stream of incoming ambient air that is drawn through the electronic vaping device 60 during vaping, which in turn heats the pre-vapor formulation by convection.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure.

It will now be apparent that a new, improved, and non-obvious electronic vaping device has been described in this specification with sufficient particularity as to be understood by one of ordinary skill in the art. Moreover, it will be apparent to those skilled in the art that modifications, variations, substitutions, and equivalents exist for features of the electronic vaping device, which do not materially depart from the spirit and scope of the example embodiments disclosed herein. Accordingly, it is expressly intended that all such modifications, variations, substitutions, and equivalents which fall within the spirit and scope of the invention as defined by the appended claims shall be embraced by the appended claims.

We claim:

1. An electronic vaping device comprising:
    a power supply component including,
        a power source configured to supply a current to a primary coil; and
    a cartridge, the cartridge including,
        an outer housing extending in a longitudinal direction;
        an air inlet;
        a vapor outlet;
        an air passage communicating with the air inlet and the vapor outlet;
        a reservoir;
        a heater circuit, the heater circuit including an electrically resistive heater in electrical communication with a secondary coil, the primary coil configured to induce voltage in the secondary coil to apply to the electrically resistive heater, and the primary coil configured to nest within the secondary coil, the primary coil and the secondary coil on a common axis; and
        a wick extending across the air passage, in communication with the reservoir, and configured to draw pre-vapor formulation from the reservoir towards the electrically resistive heater.

2. The electronic vaping device of claim 1, wherein the primary coil is a helix extending in one of the longitudinal direction of a second outer housing and a transverse direction to the longitudinal direction of the second outer housing.

3. The electronic vaping device of claim 1, wherein the electrically resistive heater has a greater electrical resistance than the secondary coil.

4. The electronic vaping device of claim 1, wherein the primary coil further comprises:
    a cylindrical core comprising a ferrite material, the primary coil being wound about the core and the core extending in the longitudinal direction of the outer housing or in a transverse direction perpendicular to the longitudinal direction of the outer housing.

5. The electronic vaping device of claim 1, wherein the power source of the power supply component is a battery and the power supply component further comprises:
    control circuitry including a rectifier circuit and a storage circuit, the rectifier circuit configured to rectify a voltage induced in the primary coil such that the storage circuit may charge the battery when the primary coil is within an inductive field.

6. The electronic vaping device of claim 1, further comprising a control circuitry, the control circuitry including an oscillator configured to oscillate power supplied to the primary coil.

7. The electronic vaping device of claim 6, wherein the primary coil is powered by the power source via the oscillator at a frequency ranging from about 100 kHz to about 1 MHz.

8. The electronic vaping device of claim 5, wherein the control circuitry further includes a voltage regulator configured to control a voltage across the primary coil.

9. The electronic vaping device of claim 5, wherein the control circuitry is configured to adjust one or more of frequency and magnitude in response to a reading of a battery voltage.

10. The electronic vaping device of claim 1, wherein at least one of the electrically resistive heater and the secondary coil are made of a magnetic material.

* * * * *